(12) United States Patent
Sweeney et al.

(10) Patent No.: US 11,553,950 B2
(45) Date of Patent: Jan. 17, 2023

(54) LAG SCREW SYSTEMS AND NAIL SYSTEMS AND METHODS INCORPORATING THE SAME

(71) Applicant: Spinal Generations LLC, Mokena, IL (US)

(72) Inventors: Patrick J. Sweeney, Flossmoor, IL (US); Matthew V. Leyden, St. Paul, MN (US)

(73) Assignee: Spinal Generations, LLC, Mokena, IL (US)

( * ) Notice: Subject to any disclaimer, the term of this patent is extended or adjusted under 35 U.S.C. 154(b) by 0 days.

(21) Appl. No.: 17/446,352

(22) Filed: Aug. 30, 2021

(65) Prior Publication Data

US 2022/0125491 A1 Apr. 28, 2022

Related U.S. Application Data

(60) Provisional application No. 63/106,182, filed on Oct. 27, 2020.

(51) Int. Cl.
*A61B 17/74* (2006.01)
*A61B 17/56* (2006.01)

(52) U.S. Cl.
CPC ...... *A61B 17/744* (2013.01); *A61B 2017/564* (2013.01)

(58) Field of Classification Search
CPC ...... A61B 17/72; A61B 17/7233–7275; A61B 17/74–748
See application file for complete search history.

(56) References Cited

U.S. PATENT DOCUMENTS 6,443,954 B1 9/2002 Bramlet et al.
9,204,910 B2 12/2015 Epperly
(Continued)

FOREIGN PATENT DOCUMENTS

JP H0966060 A 3/1997
WO 2012099944 A1 7/2012

OTHER PUBLICATIONS

Communication—Extended European Search Report, European Patent Application No. 21202042.4, dated Mar. 2, 2022.
(Continued)

*Primary Examiner* — Eduardo C Robert
*Assistant Examiner* — Michelle C Eckman
(74) *Attorney, Agent, or Firm* — Saul Ewing LLP; Brian R. Landry

(57) ABSTRACT

A trochanteric fracture nail system includes: a trochanteric fracture nail and a lag screw system adapted and configured for fixation medially through the trochanteric fracture nail. The trochanteric fracture nail includes: a substantially cylindrical wall defining a longitudinal bore; at least one lateral bore intersecting the longitudinal bore; and a detent on an inner surface of at least one of the at least one lateral bore. The lag screw system includes a lag screw and an interference member. The lag screw includes: an annular body defining a substantially hollow central bore; and a keel located along the annular body. The keel is adapted and configured to substantially lie within an outer profile of the annular body when in a neutral position. The interference member is adapted and configured to displace the keel radially to resist motion of the annular body by engaging with the detent of the trochanteric fracture nail.

5 Claims, 5 Drawing Sheets

(56) References Cited

U.S. PATENT DOCUMENTS

| | | | |
|---|---|---|---|
| 11,020,158 B2 | 6/2021 | Epperly et al. | |
| 2006/0149247 A1* | 7/2006 | Frigg | A61B 17/744 606/64 |
| 2009/0326534 A1 | 12/2009 | Yamazaki et al. | |
| 2012/0059428 A1* | 3/2012 | Epperly | A61B 17/7225 606/310 |
| 2012/0191092 A1* | 7/2012 | Buettler | A61B 17/8891 606/64 |
| 2015/0032110 A1* | 1/2015 | Boraiah | A61B 17/748 606/64 |
| 2021/0137575 A1 | 5/2021 | Epperly et al. | |

OTHER PUBLICATIONS

Wikipedia, "Drywall anchor", https://en.wikipedia.org/wiki/Drywall_anchor, downloaded Aug. 25, 2021, 2 pages.

* cited by examiner

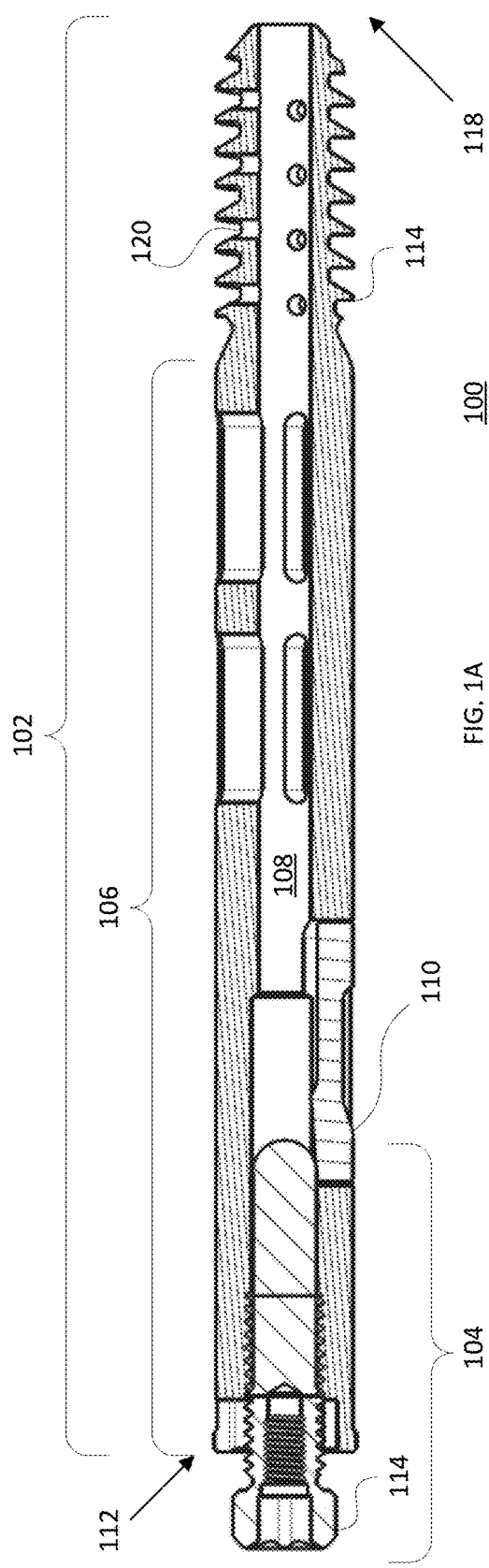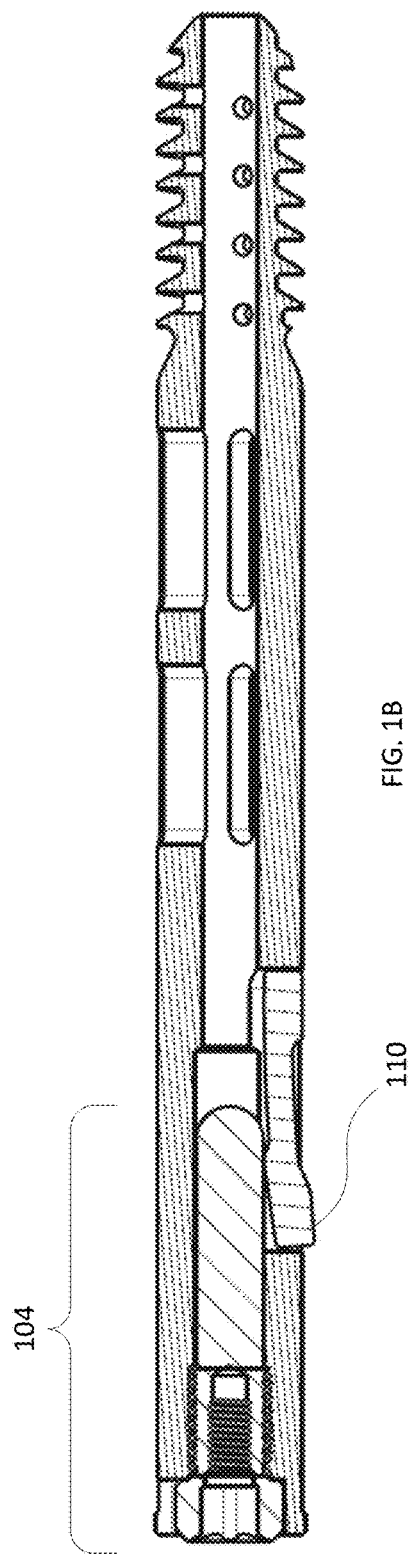
FIG. 1A
FIG. 1B

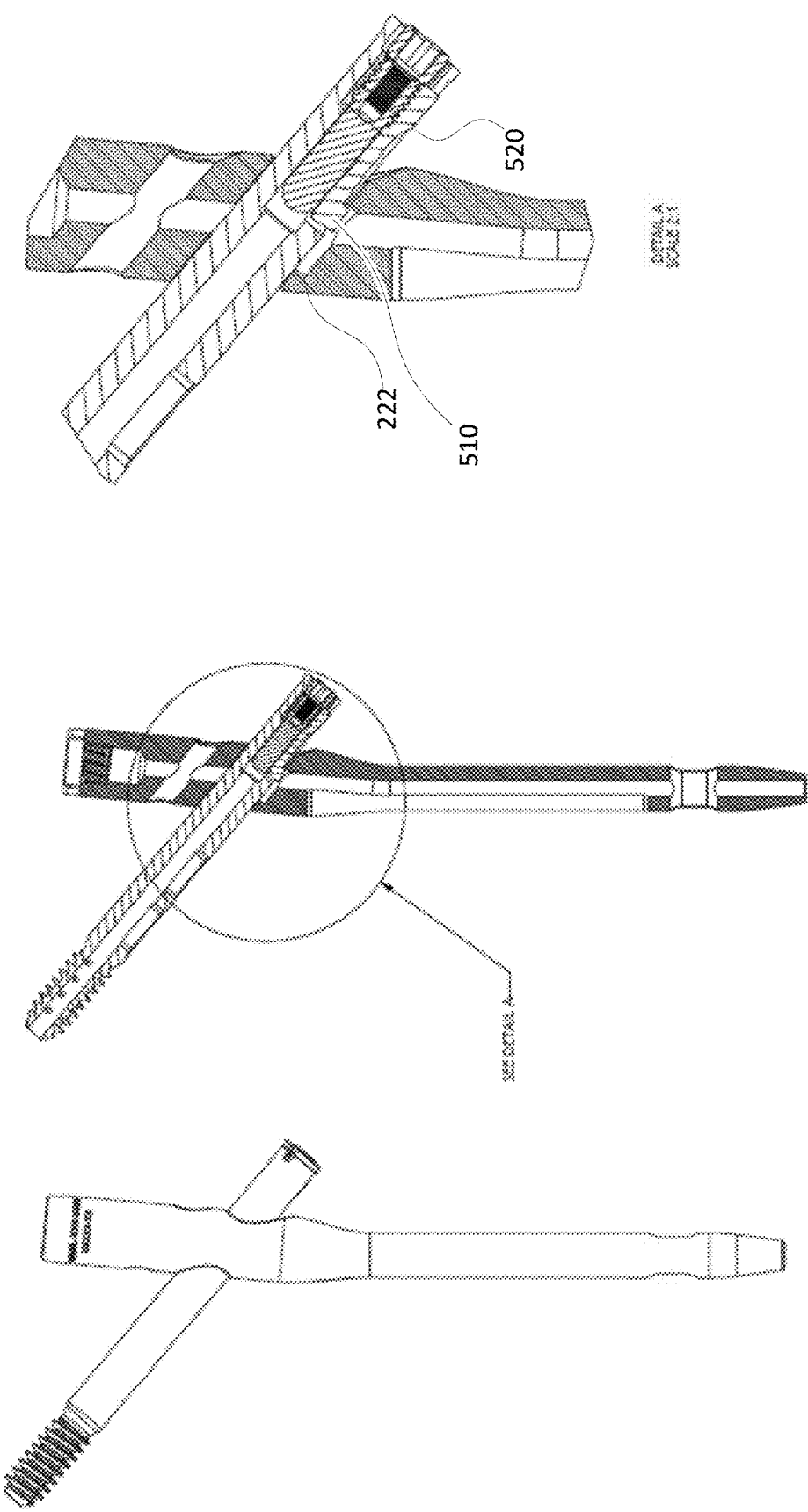

LAG SCREW SYSTEMS AND NAIL SYSTEMS AND METHODS INCORPORATING THE SAME

CROSS-REFERENCE TO RELATED APPLICATION

This application claims the benefit of priority under 35 U.S.C. § 119(e) of U.S. Provisional Patent Application Ser. No. 63/106,182, filed Oct. 27, 2020. The entire content of this application is hereby incorporated by reference herein.

BACKGROUND OF THE INVENTION

Proximal femoral fractures are serious injuries that often require surgery to repair. While the type of surgery depends on the location and severity of the fracture, the alignment of the broken bones, and the age and underlying health conditions of the patient, internal nails and screws are frequently used at the site of the fracture.

SUMMARY OF THE INVENTION

One aspect of the invention provides a trochanteric fracture nail system including: a trochanteric fracture nail and a lag screw system adapted and configured for fixation medially through the trochanteric fracture nail. The trochanteric fracture nail includes: a substantially cylindrical wall defining a longitudinal bore therewithin; at least one lateral bore intersecting the longitudinal bore; and a detent on an inner surface of at least one of the at least one lateral bore. The lag screw system includes a lag screw and an interference member. The lag screw includes: an annular body defining a substantially hollow central bore; and a keel located along the annular body. The keel is adapted and configured to substantially lie within an outer profile of the annular body when in a neutral position. The interference member is adapted and configured to: be received within the substantially hollow central bore; and displace the keel radially to resist motion of the annular body by engaging with the detent of the trochanteric fracture nail.

This aspect of the invention can have a variety of embodiments. The interference member can include male threads. The lag screw can include complementary female threads at a lateral end.

The interference member can include female threads. The lag screw system can further include: a further interference member adapted and configured to be threaded received within the interference member. The interference member can expand radially as the further interference member is advanced therein.

The lag screw can further include male threads. The male threads can be located at medial end of the lag screw.

Another aspect of the invention provides a method of treating a proximal femoral fracture in a subject in need of treatment. The method includes: placing the trochanteric fracture nail as described herein axially within the subject's femur; driving the lag screw as described herein through the femur and through the trochanteric fracture nail; and driving the interference member within the lag screw to displace the keel radially to engage with the detent the trochanteric fracture nail and resist motion of the annular body.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views.

FIGS. 1A and 1B provide cross-sectional views of a lag screw in a neutral and deployed position, respectively, according to an embodiment of the invention.

FIG. 5 provides several views of a trochanteric fracture nail system according to another embodiment of the invention.

DEFINITIONS

Figure 2:
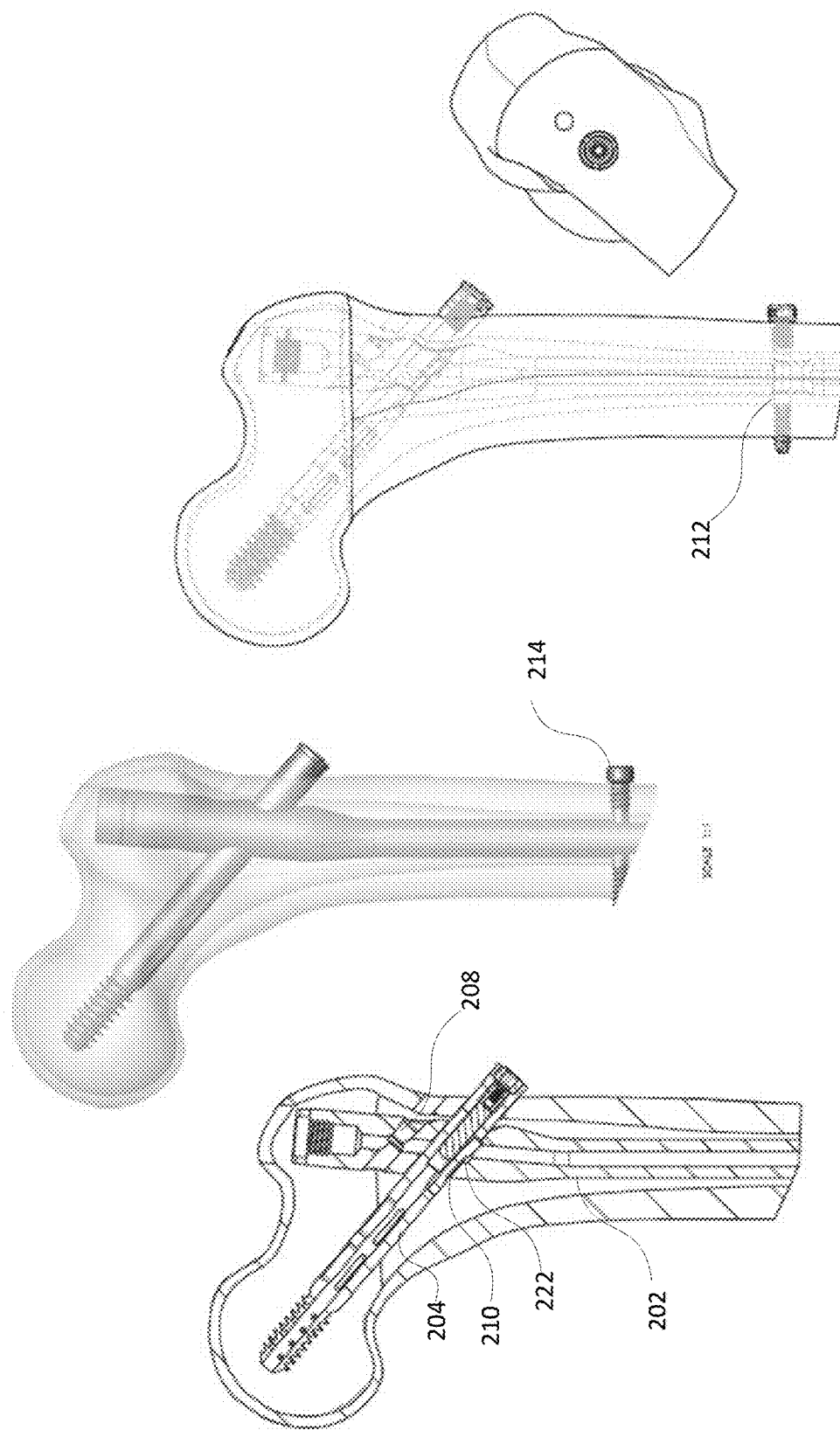
FIG. 2 provides several views of a trochanteric fracture nail system according to an embodiment of the invention.

The instant invention is most clearly understood with reference to the following definitions.

As used herein, the singular form "a," "an," and "the" include plural references unless the context clearly dictates otherwise.

As used in the specification and claims, the terms "comprises," "comprising," "containing," "having," and the like can have the meaning ascribed to them in U.S. patent law and can mean "includes," "including," and the like.

As used herein, the term "lateral" refers to a component that is located relatively away from the midline of a subject's body.

As used herein, the term "medial" refers to a component that is located relatively toward the midline of a subject's body.

Unless specifically stated or obvious from context, the term "or," as used herein, is understood to be inclusive.

DETAILED DESCRIPTION OF THE INVENTION

Trochanteric fracture nails are frequently used in the treatment of a proximal femoral fracture. Trochanteric fracture nails, including a lag screw, are universally designed as dynamic constructs allowing the lag screw, embedded in the femoral head of a patient, to collapse down into the nail as the fracture compresses.

Lag Screw System

Referring to FIGS. 1A and 1B, an embodiment of the invention provides a lag screw system 100 including a lag screw 102 and an interference member 104.

The lag screw 102 can include an annular body 106 defining a substantially hollow bore 108 and a keel 110 located along the annular body 106. The keel 110 can substantially lie within an outer profile of the annular body 106 when in a neutral position as depicted in FIG. 1A.

Keel 110 can have a bent or convex geometry such that a portion protrudes into bore 108 when in a neutral position. Keel 110 can be fabricated through fabricated through various techniques including stamping, cold-forming, pressing, machining, casting, and the like. In some embodiments, the keel is welded, fastened, bonded, and the like to the lag screw 102.

Referring to FIG. 5, keel 510 can be displaced outwardly from a lateral attachment point 520 (e.g., a hinge such as a living hinge) instead of the medial attachment point depicted in FIGS. 1A-2. The embodiment depicted in FIGS. 1A-2 experiences a compression load as the screw 204 slides laterally inside the nail 202, causing it to lock. The embodiment depicted in FIG. 5 is positioned laterally (in comparison) and the "hook" locks down into the nail 202 with a tensile force being exerted on it as the screw slides laterally.

The benefit of the embodiment depicted in FIG. 5 is that keel 510 is positioned in the screw 204 where the least forces are transmitted when the screw 204 and nail 202 interact and thus there will be less damage to the device as it wears. The screw 204 has vertical forces exerted on its tip when the patient is standing. These forces cause the screw 204 to push down on the medial edge of the nail hole and pivot upwards at the lateral hole. The inferior lateral portion of the screw 204 and the nail hole is subject to the least stress in comparison to the inferomedial portions. For the avoidance of doubt, both embodiments are viable.

The interference member 104 can be adapted and configured to be received within the substantially hollow central bore 108. The interference member 104 can be cannulated so that the interference member 104 can slide over a guidewire, either independently and/or as part of a pre-assembled lag screw system 100, e.g., in the neutral state depicted in FIG. 1A (but without cannulation of the interference member 104).

As depicted in FIG. 1B, when the interference member 104 is advanced medially, the medial end of the interference member 104 presses against the keel 110 to displace it radially to resist motion of the annular body 106 (e.g., rotationally and/or laterally). In some embodiments, the keel 110 can be positioned along the lag screw 102 such that the keel 110 will lie within a trochanteric nail 202 and press against the trochanteric nail when displaced radially as depicted in FIG. 2.

The interference member 104 can be retained medially after engaging the keel 110. In one embodiment, the interference member 104 can include threads (e.g., male threads) that engage with complementary female threads at a lateral end 112. Threads advantageously facilitate removal of the interference member 104 if desired. In another embodiment, the interference member can be retained medially through interference, one or more detents, adhesives, and the like. The keel 110 can have shape memory and/or be biased to facilitate its return to a neutral position and/or the geometry of the keel 110 and/or the interior of the trochanteric fracture nail 202 can push the keel 110 centrally as the lag screw 102 is rotated (e.g., in the anti-driving direction).

In still another embodiment, the interference member 104 can be retained medially by a further interference member 114. The further interference member 114 can be advanced medially within the interference member 104 to cause the interference member 104 to expand radially to form a tighter fit with substantially hollow central bore 108. For example, the interference member can include one or more lateral slits that facilitate radial expansion. In one embodiment, the further interference member 114 can include male threads that cooperate with complementary female threads on interference member 104.

Lag screw 102 can include threads 116 (e.g., male threads), e.g., on medial end 118. The threads can be engineered (e.g., through pitch, coarseness, angle, major and minor diameters, and the like) for engagement with bone as depicted in FIG. 2. For example, lag screw 102 can be a self-tapping screw.

Lag screw 102 can include one or more radial holes 120 that can be utilized, e.g., for injection of therapeutics, biologics, and the like, e.g., as discussed in Applicant's U.S. Patent Application Publication No. 2016/0008044.

Trochanteric Fracture Nail System

Figure 3:
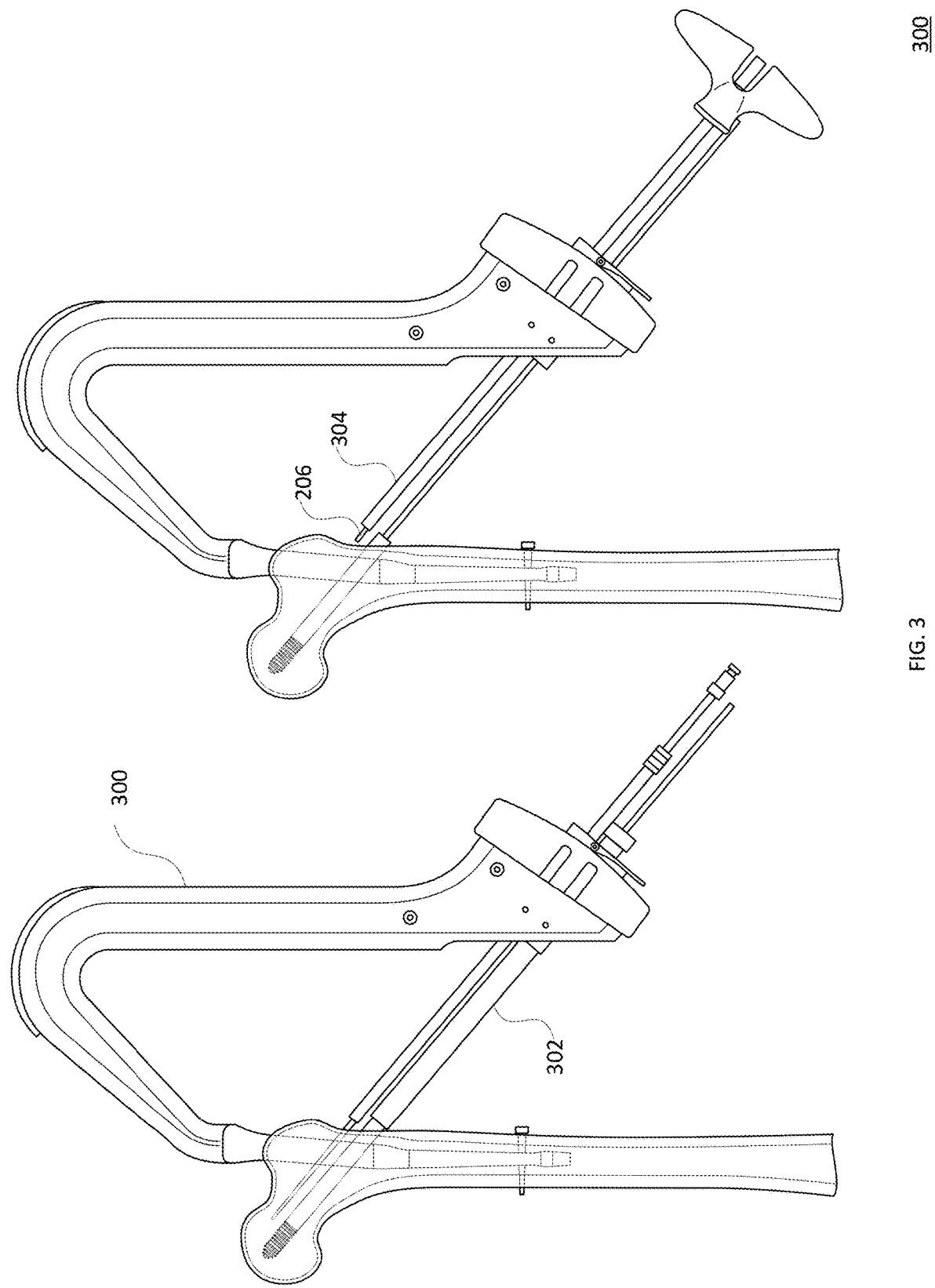
FIG. 3 provides several views of a trochanteric fracture nail system and guide according to an embodiment of the invention.

Referring to FIGS. 2 and 3, a trochanteric fracture nail system 200 is provided. Trochanteric fracture nail system 200 includes a trochanteric fracture nail 202, a lag screw 204 adapted and configured for fixation medially through the trochanteric fracture nail 202. As depicted in FIG. 3, the trochanteric fracture nail system 200 can optionally include a laterally inserted screw 206 adapted and configured for fixation medially through the trochanteric fracture nail.

Lag screw 204 and laterally inserted screw 206 can be adapted for fixation parallel to each other (e.g., to resist rotation of the trochanteric fracture nail 202). In some embodiments, trochanteric fracture nail 202 includes a first parallel bore 208 and a second parallel bore 210. Lag screw 204 may be inserted through second parallel bore 210 and laterally inserted screw 206 (depicted in FIG. 3) may be inserted through first parallel bore 208 through the femur of a subject in need thereof. In certain embodiments, trochanteric fracture nail 202 further comprises a third bore 212 distal to first parallel bore 208 and second parallel bore 210. A medical-grade screw 214 may be inserted through the femur of a subject in need thereof, through third bore 212, and through the opposite side of the subject's femur in order to provide additional support to a proximal femoral fracture during healing. In some embodiments, laterally inserted screw 206 comprises one or more threads (e.g., machine threads), which can be threaded into trochanteric fracture nail 202.

The second parallel bore 210 of trochanteric fracture nail 202 can include a detent 222 adapted and configured to receive keel 110. The detent 222 can have a complementary geometry to the keel 110 in order to prevent or limit axial and or rotational movement of the lag screw 102, 204. As will be appreciated, tolerances between the keel 110 and the detent 222 can be engineered to balance prevention of undesired movement with ease of engagement. In some embodiments, the detent 222 is parallel with bore 210. The detent 222 can extend fully across the trochanteric fracture nail 202 or can be closed on one or both ends by the wall of the trochanteric fracture nail 202 (thereby limiting axial movement).

Referring now to FIG. 3, in some embodiments, trochanteric fractur nail system 200 further includes a guide 300. FIG. 3 depicts trochanteric fracture nail system 200 with the guide 300 engaged (e.g., through threading) to the superior end of the trochanteric fracture nail 202. The guide 300 can include parallel bores for placement of lag screw 204 and laterally inserted screw 206 through a subject's femur and through trochanteric fracture nail 202. In some embodiments, a sheath 302, 304 may be inserted into the parallel bores of the guide before placement of lag screw 204 and laterally inserted screw 206. In some embodiments, the sheath may act to hold lag screw 204 and laterally inserted screw 206 in a desired position as the screws are placed through a subject's femur and through trochanteric fracture nail 202. The guide may be adapted and configured to engage with a superior end of the trochanteric fracture nail.

Materials

The components described herein can be made of any biocompatible material known to a person of skill in the art. In some embodiments, one or more components are made from a biocompatible metal. Exemplary biocompatible metals include, but are not limited to, stainless steel, titanium, aluminum, titanium alloy, cobalt-chromium alloy, and combinations thereof. In another embodiment, one or more components are made from a biocompatible plastic. Exemplary biocompatible plastics include, but are not limited to, polyvinyl chloride (PVC), polyethylene, polycarbonate, polyether ether ketone (PEEK), polyetherimide (PEI), polypropylene, polysulfone, polyurethane, and combinations thereof.

Screw Drives

One or more of lag screw 102, interference member 104, and further interference member 114 can include a screw drive (e.g., at lateral end 112) for engagement with a screw driver (e.g., an. Exemplary screw drive geometries include, pyramid-shaped inlet is shown and certain embodiments may include alternative shapes, for example hexagonal. Other suitable drives include slotted, cross, cruciform, Phillips, Frearson, French recess, JIS B 1012, Mortorq, Pozidriv PV, Supadriv PZ, Torq-set, Phillips/slotted, external polygon, square, pentagonal, hexagonal, 12-point, internal polygon, triangle, Robertson, hexagonal (Allen), double square, triple square, 12-spline flange, double hex, star (e.g., TORX®, TORX PLUS®), Polydrive, three-pointed, tri-point, tri-groove, tri-wing, Bristol, Quadrex, Pentalobe, spanner (pig nose), and the like.

Method of Treating a Proximal Femoral Fracture

Figure 4:
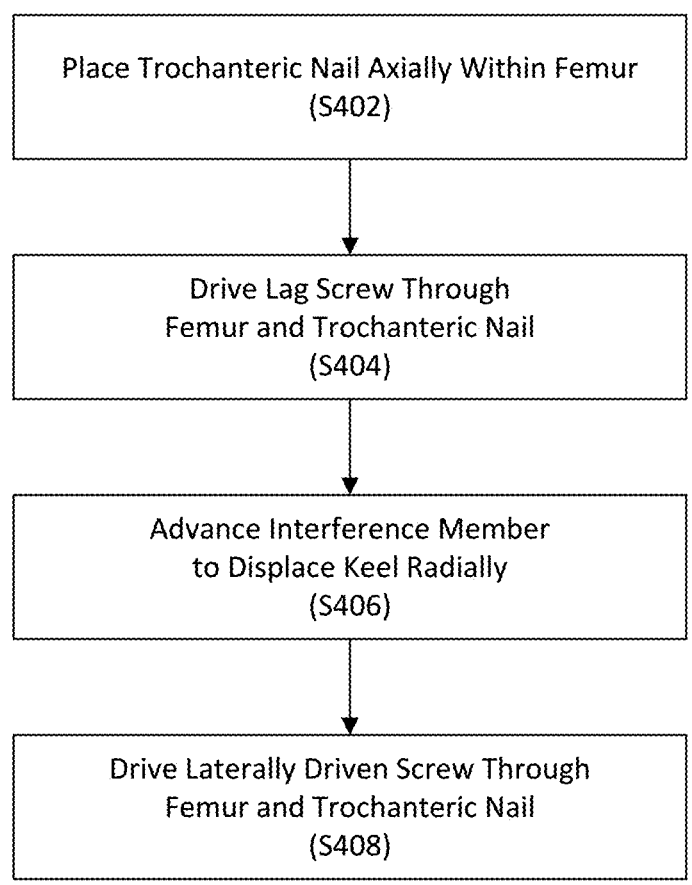
FIG. 4 depicts a method of treating a proximal femoral fracture in a subject in need thereof in accordance with a preferred embodiment of the invention.

A flowchart depicting an exemplary method of treating a proximal femoral fracture in a subject in need thereof is shown in FIG. 4.

In step S402, a trochanteric fracture nail is placed axially within a subject's femur (e.g., after boring with a surgical drill bit). The trochanteric fracture nail can be nail 102. In some embodiments, a superior end of nail 102 is engaged with a guide as described herein (either before or after placement of the trochanteric fracture nail).

In step S404, a lag screw is driven through the femur and through the trochanteric fracture nail. In some embodiments, lag screw 104 is driven through trochanteric fracture nail 102. In some embodiments, lag screw 104 is driven through second parallel bore 110 of nail 102. In certain embodiments, the lag screw is advanced through a first parallel bore of a guide that is engaged with a superior end of the trochanteric fracture nail. A guidewire and/or imaging (e.g., fluoroscopy) can be utilized to confirm accurate placement of a bore and associated lag screw.

In step S406, an interference member can be advanced to displace a keel radially from the lag screw. The keel can be deployed within the trochanteric fracture nail and can resist rotational and/or lateral movement of the lag screw.

In step S408, a laterally inserted screw can be driven through the femur and through the trochanteric fracture nail. The laterally inserted screw can be screw 106. In some embodiments, laterally inserted screw 206 is driven through trochanteric fracture nail 202. In some embodiments, laterally inserted screw 106 is driven through first parallel bore 208 of nail 202. In certain embodiments, the laterally inserted screw is advanced through a second parallel bore of a guide that is engaged with a superior end of the trochanteric fracture nail. A guidewire and/or imaging (e.g, fluoroscopy) can be utilized to confirm accurate placement of a bore and associated laterally inserted screw.

In some embodiments, the exemplary method further comprises the step of inserting a medical grade screw through the femur of a subject in need thereof, through a third bore in the trochanteric fracture nail, and through the opposite side of the subject's femur. In certain embodiments, the medical grade screw may provide additional support to the proximal femoral fracture during healing.

In embodiments wherein a guide is engaged to the superior end of the trochanteric fracture nail during the exemplary method, at the completion of step S408, the guide can be disengaged from the superior end of the nail after the lag screw and laterally inserted screw are advanced.

EQUIVALENTS

Although preferred embodiments of the invention have been described using specific terms, such description is for illustrative purposes only, and it is to be understood that changes and variations may be made without departing from the spirit or scope of the following claims.

INCORPORATION BY REFERENCE

The entire contents of all patents, published patent applications, and other references cited herein are hereby expressly incorporated herein in their entireties by reference.

The invention claimed is:

1. A trochanteric fracture nail system comprising:
 a trochanteric fracture nail comprising:
  a substantially cylindrical wall defining a longitudinal bore therewithin;
  at least one lateral bore intersecting the longitudinal bore; and
  a detent on an inner surface of at least one of the at least one lateral bore; and
 a lag screw system adapted and configured for fixation medially through the trochanteric fracture nail, the lag screw system comprising:
  a lag screw comprising:
   an annular body defining a substantially hollow central bore; and
   a keel located along the annular body, the keel adapted and configured to substantially lie within an outer profile of the annular body when in a neutral position; and
  an interference member adapted and configured to:
   be received within the substantially hollow central bore; and
   displace the keel radially to resist motion of the annular body by engaging
  with the detent of the trochanteric fracture nail;
 wherein:
  the interference member comprises female threads; and
  the lag screw system further comprises:
   a further interference member adapted and configured to be threaded received within the interference member;
   wherein the interference member expands radially as the further interference member is advanced therein.

2. The trochanteric fracture nail system of claim 1, wherein:
 the interference member further comprises male threads; and
 the lag screw further comprises complementary female threads at a lateral end.

3. The trochanteric fracture nail system of claim 1, wherein the lag screw further comprises:
 male threads.

4. The trochanteric fracture nail system of claim 3, wherein the male threads are located at medial end of the lag screw.

5. A method of treating a proximal femoral fracture in a subject in need of treatment, the method comprising:
 placing the trochanteric fracture nail of claim 1 axially within the subject's femur;

driving the lag screw according to claim 1 through the femur and through the trochanteric fracture nail; and driving the interference member within the lag screw to displace the keel radially to engage with the detent the trochanteric fracture nail and resist motion of the annular body.

\* \* \* \* \*